United States Patent [19]

Ensanian

[11] 4,006,063
[45] Feb. 1, 1977

[54] METHOD FOR MEASURING SURFACE CHARACTERISTICS OF METALS AND METALLOIDS

[76] Inventor: Minas Ensanian, P.O. Box 98, Eldred, Pa. 16731

[22] Filed: May 5, 1975

[21] Appl. No.: 574,360

Related U.S. Application Data

[63] Continuation of Ser. No. 79,033, Oct. 8, 1970, abandoned.

[52] U.S. Cl. .................. 204/1 T; 204/195 R; 324/29; 324/65 R; 324/65 P; 324/71 R
[51] Int. Cl.² .................. G01N 27/46
[58] Field of Search .......... 204/1 T, 195 R; 324/65 R, 65 P, 71 R, 29, 30 R

[56] References Cited

UNITED STATES PATENTS

| | | | |
|---|---|---|---|
| 2,183,531 | 12/1939 | Allison | 204/195 R X |
| 2,506,454 | 5/1950 | Holmwood | 324/65 R |
| 2,531,747 | 11/1950 | Stearn | 204/195 |
| 2,560,792 | 7/1951 | Gibney | 204/56 R X |
| 3,034,050 | 5/1962 | Yuen | 324/71 R |
| 3,282,804 | 11/1966 | Stearn | 204/1 T |
| 3,530,045 | 9/1970 | Alburger | 204/1 T |
| 3,551,801 | 12/1970 | Wood et al. | 324/29 |
| 3,808,105 | 4/1974 | Rozeanu | 204/1 T |

FOREIGN PATENTS OR APPLICATIONS 1,044,532  10/1966  United Kingdom .......... 204/195 R

OTHER PUBLICATIONS

Webster's Seventh New Collegiate Dictionary, p. 17, (1963).

*Primary Examiner*—G. L. Kaplan
*Attorney, Agent, or Firm*—Ashlan F. Harlan, Jr.

[57] ABSTRACT

A process applicable to metal and metalloid surfaces for detecting and determining the boundaries of stressed areas and areas exhibiting chemical variations involves ascertaining at a number of points on a surface the electrical potential generated between the surface and an electrode when both are in contact with a solution of an electrolyte. The surface and electrode may be of the same material or different and the electrolyte may be a soluble salt of the same metal as either the surface or the electrode or of another metal. The testing can be carried out by hand or automatically. Apparatus suitable for carrying out the tests is disclosed, such apparatus including means for testing individual points or for obtaining one or more continuous readings of the generated potential across the surface.

12 Claims, 14 Drawing Figures

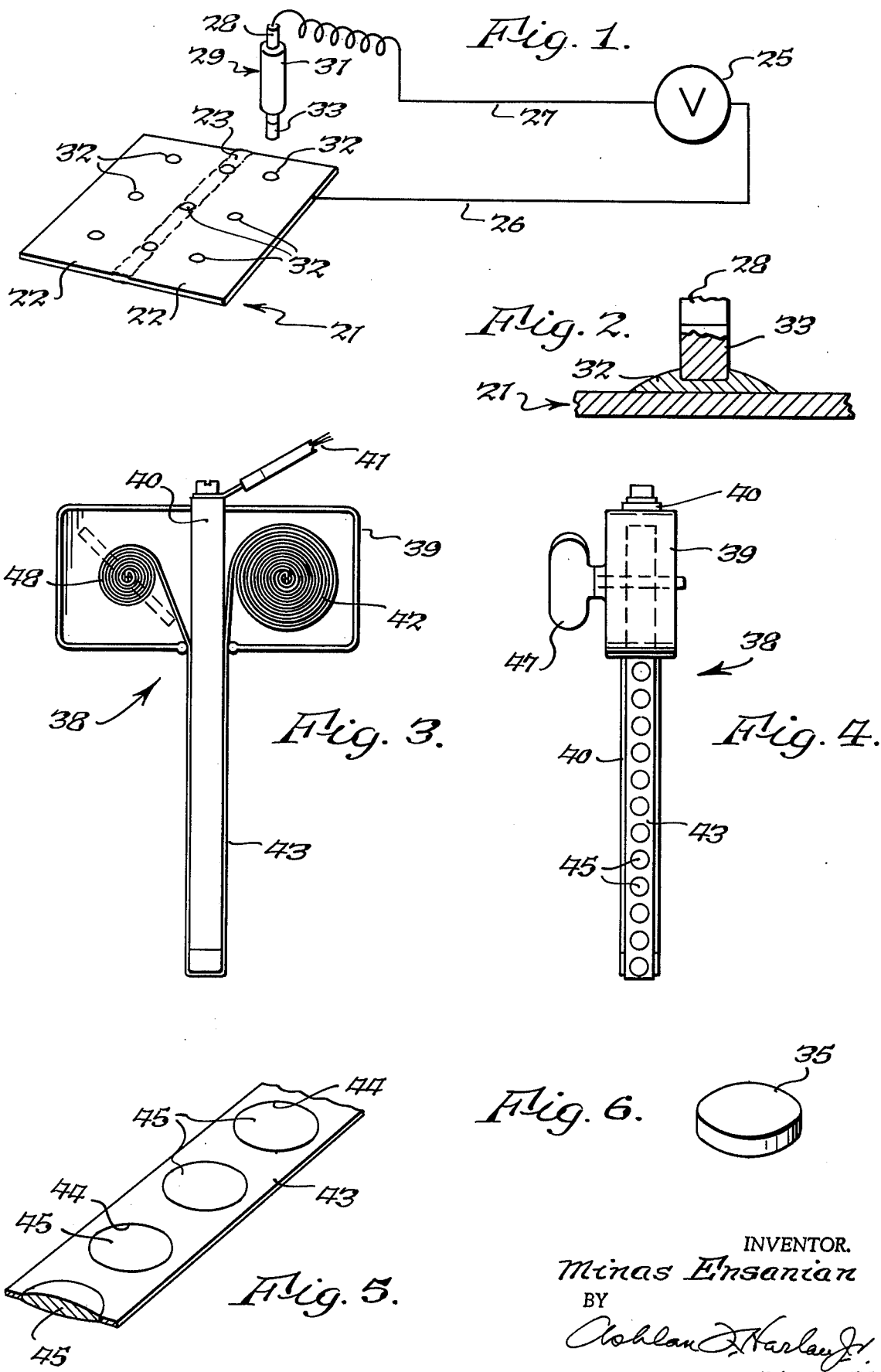

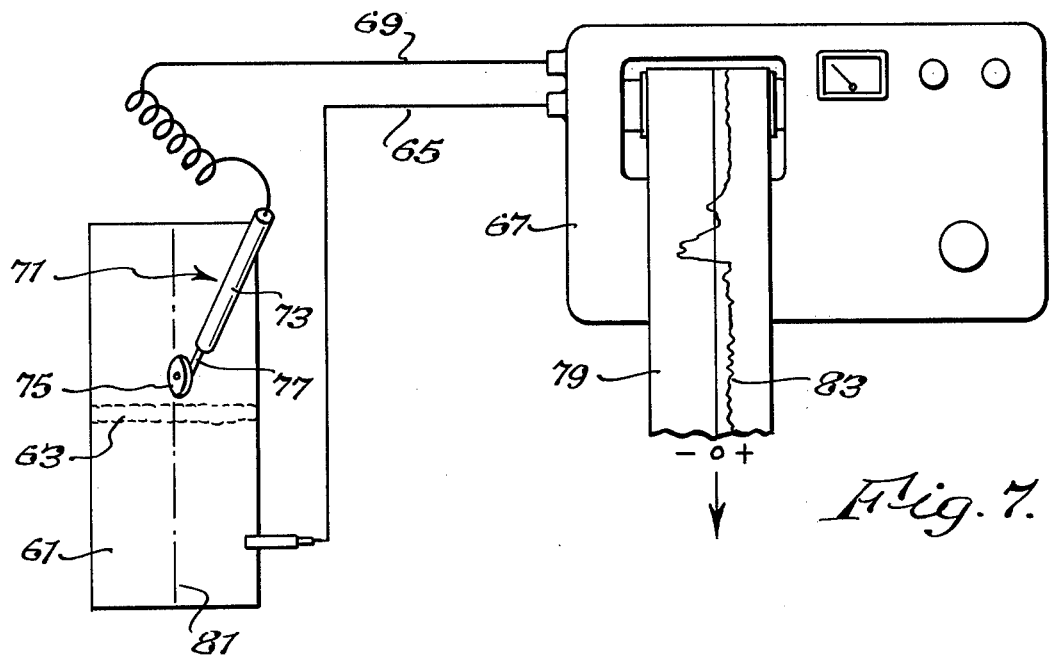
Fig. 7.
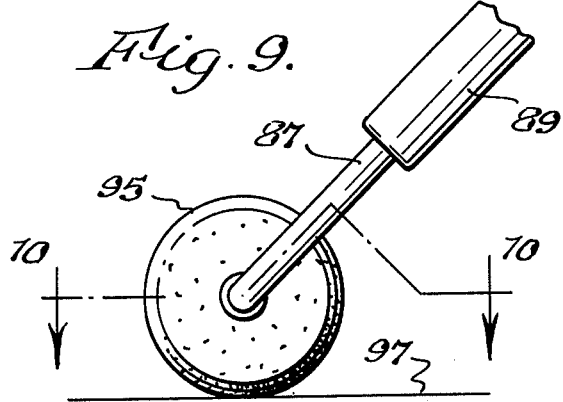
Fig. 9.
Fig. 8.
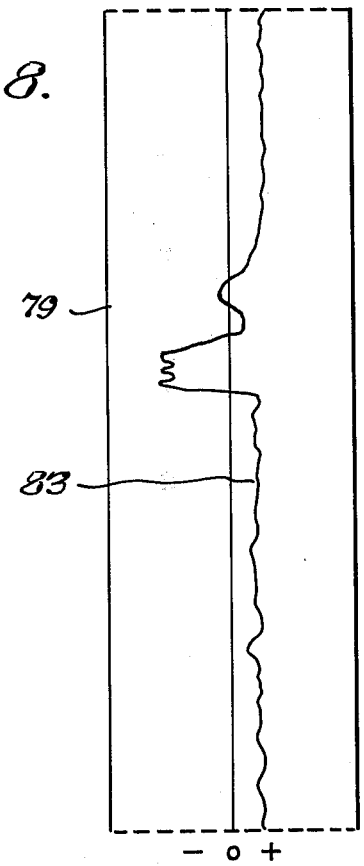
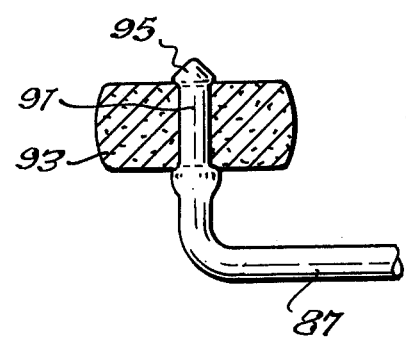
Fig. 10.

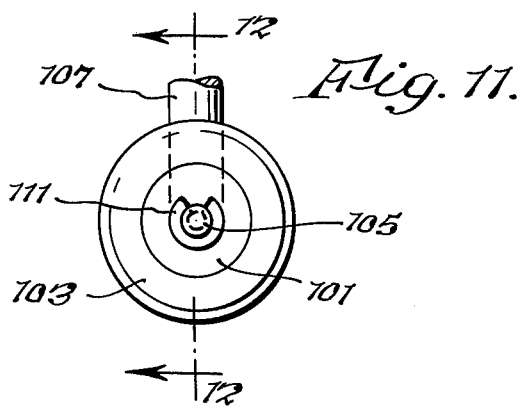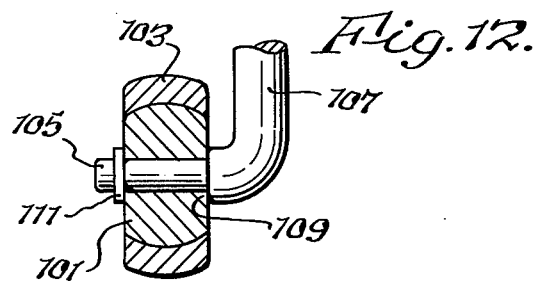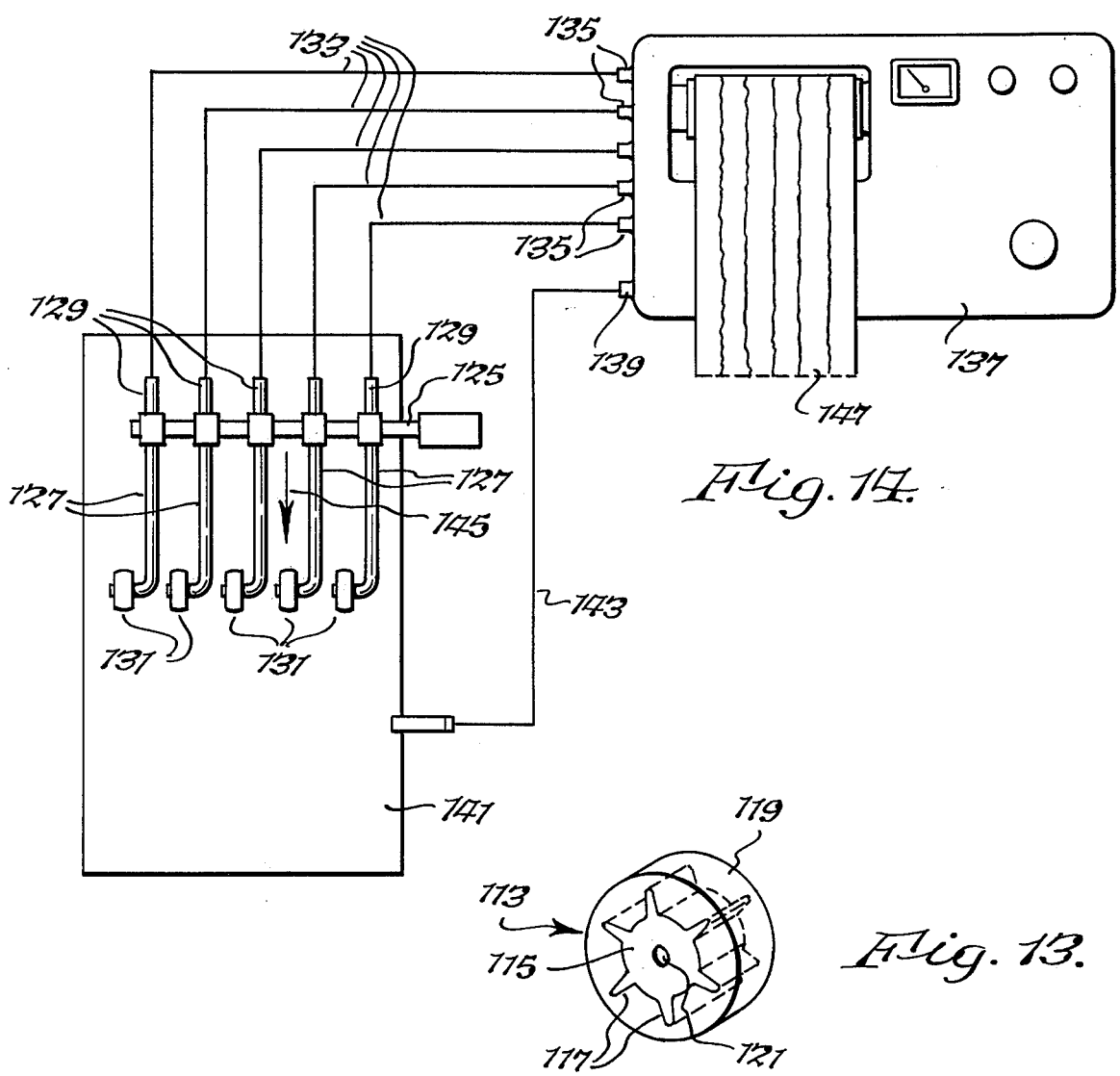

METHOD FOR MEASURING SURFACE CHARACTERISTICS OF METALS AND METALLOIDS

This is a continuation of application Ser. No. 79,033, filed Oct. 8, 1970, and now abandoned.

BACKGROUND OF THE INVENTION

This invention is concerned with the surfaces of metals and metalloids and particularly relates to a method of detecting and measuring and/or comparing chemical and physical characteristics of such surfaces and with apparatus for performing such a method.

It is known that no two objects, whether they are natural or artificial, are idential in all respects. In at least some one or more respects, they differ. The differences may lie in shape, size, color, internal structure, chemical composition, both internal and external, and other items. In many cases, means exist for determining and/or comparing such differences. However, except for such easily determined differences as those in color, reflectivity and roughness or smoothness, no means has been available until now for detecting and measuring the differences in the surfaces of metals and metalloids resulting from internal stresses and surface chemistry variations. The last mentioned differences may be caused by, among other factors, differences in cooling rates, localized heating, mechanical treatment and environmental factors.

Since the behavior of a metal in many uses, such as electroplating, adhesive bonding, and deep drawing, for example, is affected by its surface characteristics, it is important to be able to detect differences in such characteristics and determine, i.e. map out, the areas affected. With metalloids, also, surface differences are in some cases important and the determination of the degree of difference and/or the area involved are desirable.

SUMMARY OF THE INVENTION

The present invention provides a process applicable to metal and metalloid surfaces for detecting and determining the boundaries of stressed areas and areas exhibiting chemical variations. This is accomplished by ascertaining the mechanogalvanic potential at a number of points on the surface of the specimen since it has been found that the mechanogalvanic potential at a point on the surface is influenced by surface chemistry and/or by localized stresses in the specimen adjacent said point. The invention also comprehends apparatus suitable for comparing the stresses and chemistry at different points on a metal or metalloid surface so that the different surface areas, for example, in a metal sheet, may be charted or mapped.

SHORT DESCRIPTION OF THE DRAWINGS

FIG. 1 is a partially schematic view showing a very simple apparatus for determining mechanogalvanic potential;

FIG. 2 is an enlarged, sectional detail view of the apparatus illustrated in FIG. 1 showing the electrode and surface closely adjacent but separated by electrolyte;

FIG. 3 is a schematic front view of a probe equipped with a supply of electrolyte elements;

FIG. 4 is a side view of the probe illustrated in FIG. 3;

FIG. 5 is an enlarged, fragmentary perspective view of a tape carrying electrolyte pads or elements suitable for use with the probe shown in FIGS. 3 and 4;

FIG. 6 is an enlarged perspective view of a disc containing an electrolyte;

FIG. 7 is a partially schematic view of apparatus for measuring and comparing the mechanogalvanic potential at successive points along the surface of a metal or metalloid object;

FIG. 8 is an enlarged, fragmentary view of the recording tape employed with the apparatus of FIG. 7;

FIG. 9 is a fragmentary side view of probe with a rolling electrolyte carrier suitable for use in the apparatus illustrated in FIG. 7;

FIG. 10 is a sectional view on line 10—10 of FIG. 9;

FIG. 11 is a side view of another form of rolling electrolyte carrier;

FIG. 12 is a sectional view on line 12—12 of FIG. 11;

FIG. 13 is a perspective view of still another form of electrode carrier; and

FIG. 14 is a schematic view similar to FIG. 7 but illustrating apparatus adapted to obtain a plurality of simultaneous continuous readings of the mechanogalvanic potential at different points on a metal or metalloid surface.

DETAILED DESCRIPTION OF THE INVENTION

In carrying out the process of the present invention, advantage is taken of the fact that there is a small electrical voltage generated when two electrodes are first placed in a solution of a soluble metal salt (an electrolyte). When both electrodes are of the same metal and the electrolyte is also a salt of that metal, the voltage reflects differences in the physical and/or chemical nature of the surfaces of the electrodes. Such a voltage is hereinafter called a mechanogalvanic potential, and for convenience, is often referred to as MGP. Since differences in temperature of the electrodes, the amount of light falling thereon, and other factors may also cause voltage generation, it is important that in determining the MGP of a test specimen, so far as possible the electrodes, i.e. the surface being tested and the test probe or standard electrode, are subjected to the same conditions and that the standard electrode is as free as possible from stresses and contamination. Otherwise the test results will not accurately reflect the surface condition of the metal test specimen so that thermodynamic or theoretical calculation based thereon will be meaningless or of little value. Thus, in the following description, it will be understood without specific mention that ambient conditions are controlled to minimize errors except as otherwise stated. As hereinafter described, the mechanogalvanic potential of one or more surface points on a metal or metalliod specimen may also be determined using a standard electrode which is not of the same material as the test specimen and/or an electrolyte which is not a salt of either the metal of the test specimen or the standard electrode.

In FIG. 1 there is shown schematically a simple apparatus for determining the MGP at a number of points on the surface of a metal plate 21 which has been formed by welding together two smaller plates 22, the weld joint being indicated at 23. The apparatus comprises a millivolt meter 25 to the terminals of which leads 26 and 27 are connected. The lead 26 runs to the test specimen, the plate 21, to which it is attached by suitable means (not shown) in such manner as to obtain a good electrical contact. The lead 27 runs to and is connected electrically to one end of the standard electrode 28 of the test probe 29. The electrode 28, which may be of any desired shape and size, may be provided with an insulating handle 31 and preferably has its free end of restricted area so that a relatively small area of contact is presented for use with the test specimen. The electrolyte solution is designated by the numeral 32 and in this simple form of apparatus may be deposited as drops on the surface of the test plate 21 at various random or selected points. Desirably, the free end of the electrode 28 is provided with a separable of detachable portion 33, which may be replaced, secured by any suitable means, e.g. threads (not shown).

If a reading of the generated voltage is made as the tip 33 of the test probe electrode 28 is placed in contact with each spot or drop of electrolyte solution 32 (see FIG. 2), it can be determined which areas of the plate 21 are at the same mechanogalvanic potential and which are at a higher or lower potential than a selected point. The number of readings on a test specimen can be as large as desired since it is only necessary to provide a greater number of drops of electrolyte solution. When a large number of readings are taken on a specimen and the results are posted at points on a chart or picture of the specimens which correspond to the respective points on the specimen where the readings were obtained, much information as to the surface characteristics may be obtained.

When, as described above, drops of electrolyte solution are used, they may tend to spread out and run together or run off the test specimen. It is, therefore, usually desirable to hold the electrolyte solution in a coherent, formed body. There are a number of ways of accomplishing this. In one way, pads such as discs of absorbent paper are saturated with the desired solution of electrolyte and placed at the desired points on the surface of the test specimen. In another way, a non-ionizable gelling agent, such as gelatin, may be added to the electrolyte solution and semi-solid discs molded from the mixture. Such discs, exemplified as 35 in FIG. 6, or saturated paper discs may be placed as desired on the surface of the test specimen and readings taken by pressing the test probe electrode against or into the disc.

FIGS. 3 and 4 illustrate in schematic form a modified form of test probe which is designated to carry a supply of electrolyte-saturated, absorbent discs that can be successively fed below the electrode as readings are taken on the surface of the test specimen, and then removed and temporarily stored. Thus, excess electrolyte solution is not left on the test specimen to contaminate other specimens or damage other equipment, and readings may be taken rapidly. As illustrated, the probe 38 comprises a housing 39 and an electrode 40. The latter has a lead 41 suitably attached to its upper end, by which it may be electrically connected to a voltage measuring device such as the millivoltmeter 25 shown in FIG. 1. The housing 39, through which the electrode 40 extends, carries a roll 42 of suitable non-conductive tape 43 having a spaced series of holes 44. As best shown in FIG. 5, in each of the holes 44 of the tape 43 there is provided an absorbent pad 45 which is saturated with the desired electrolyte solution. Suitable means, such as handle 47 is provided for feeding the tape 43 from the roll 42 around the free end of the electrode 40 and winding up the tape containing used pads in a roll 48. As with the readings obtained by the simple test probe illustrated in FIG. 1, the readings obtained by use of the probe 38 in the same manner can be plotted on a chart or picture of the test specimen to facilitate visualization of the surface condition thereof. If desired, the tip of the free end of electrode 40 may be detachable and alternative means (not shown) may be provided for feeding fresh electrolyte pads to the electrode tip, such, for example, as a trigger and ratchet mechanism instead of handle 47 or a spring motor for winding up the tape 43.

In the foregoing examples of the determination of variations in mechanogalvanic potential on the surface of a metal specimen, the tests have been made at discrete points in such surface. It is clear that much more information is obtainable if the voltage of the mechanogalvanic potential is continually measured along one or more lines from one end or side of the test specimen to the other. FIG. 7 illustrates schematically a form of apparatus suitable for such measurement.

In FIG. 7 a metal plate 61 having a weld joint 63 is electrically connected by a suitably attached lead 65 to one terminal of a recording millivoltmeter 67. The other terminal of the millivoltmeter is electrically connected by lead 69 to the electrode of a test probe comprehensively designated 71. The probe 71 comprises an insulating handle 73 and a wheel 75 which serves as an electrolyte carrier and is rotatably mounted, e.g. on a metal rod 77, in such a way as to be in electrical contact with the electrode of the probe. The construction and mounting of the wheel 75 is hereinafter described more specifically. Suffice it here to say that the circumferential surface of the wheel carries electrolyte solution, for example, as a tire of gelled electrolyte solution similar to the disc 35 described above, so that in use the gelled solution is maintained between and in contact with the electrode and the test surface.

The operation of the apparatus shown in FIG. 7 is similar to that of the apparatus illustrated in FIG. 3. The differences arise from the facts that the test probe terminates in a wheel thereby enabling a continuous test to be run by rolling the wheel over the surface of the test specimen and that the recording millivoltmeter 67 produces a permanent record on the tape 79 of the mechanogalvanic potential of the test surface along the line, indicated at 81, followed by the wheel on the probe 71. FIG. 8 shows, enlarged, a portion of the tape 79 with the recorded mechanogalvanic potentials being depicted by the line 83.

In carrying out tests with a rolling electrolyte carrier and a recording millivoltmeter the recording pen of the meter is adjusted to the O line of the recording chart or tape. As shown by the line 83 on the tape 79 when the wheel rolls over the surface of the test specimen a potential is generated and recorded. The line 83 also illustrates the deviation from a normal or average base line that occurs as surface conditions on the test specimen cause variations in the MGP. Such deviations may be so great as to cause a reversal of polarity in the MGP, the tape 79 illustrating such a reversal at the area of the weld 63 on the test specimen. It will be understood that the wheel 75 may be run repeatedly over the surface of the test specimen 61 in parallel lines in any direction or in a pattern, the accumulated readings of mechanogalvanic potentials permitting accurate plotting of the surface state of the test specimen.

A large number of materials and styles of construction may be used in forming rolling wheels for test probes, such as that shown at 75 in FIG. 7, according to the invention. In FIGS. 9 and 10 a simple form is illustrated in which a metal electrode 87, having an insulating handle 89, is provided at one end with an angled, reduced portion 91 which serves as an axle for the wheel 93, the other end (not shown) of the electrode being provided with suitable means for attachment of an electrical lead. The wheel 93 carries electrolyte solution and is rotatable on the angled portion 91 of the electrode which extends through an axial bore in the wheel. Suitable means such, for example, as an enlarged portion 95 on the extremity of the axle portion 91 may serve to hold the wheel 93 in place.

The construction of wheel 93 may vary greatly, as desired. It may, for example, be constructed of fabric, either felted or woven, paper, wood, natural or synthetic sponge, or porous ceramics, in all cases being substantially saturated, when in use, with an appropriate electrolyte. In many cases, a gelled electrolyte solution, such as hereinafter described, is preferred, the gelled electrolyte solution being cast or otherwise formed into a wheel of desired size and cross-sectional configuration. It will be evident that as the wheel 93 is rolled along the test surface, represented at 97 in FIG. 9, the electrolyte therein is in contact with both the surface and the electrode.

FIGS. 11 and 12 depict another form of wheel for test probes in which a metal core or hub 101 is provided with an annular tire or rim 103 of electrolyte-carrying material. Such material may be any of those previously mentioned but, in general, tires of gelled electrolyte solution are preferred, the gel being readily molded on the core. The wheel is rotatably mounted on an axle 105 provided on one end of the metal electrode shaft 107. The latter is provided at its other end (not shown) with suitable means for connection of an electrical lead thereto and is also provided with an insulating coating or handle (not shown) for grasping. The axle 105 passes through the hub 101 and the latter, which serves as the electrode for the probe, is conveniently held on the axle against the shoulder 109 of the shaft 107 so as to make electrical contact therewith, by a removable retaining ring 111.

FIG. 13 illustrates a modification of the conductive wheel shown in FIGS. 11 and 12. In this modified wheel 113 the metal hub or core 115 is provided with radially projecting fins or webs 117 which serve to hold and support an electrolyte-containing outer portion or rim 119, which may be molded thereon. The wheel 113 may be mounted for rotation on a conducting electrode holder by the axial bore 121 through the hub electrode, in the same manner as the wheel illustrated in FIGS. 11 and 12. The rim 119 may be formed of any suitable porous material such as one of those described above. However, a gelled electrolyte solution is preferred.

When large surfaces are to be tested to map or chart the MGP at points over an extensive area, many determinations or readings must be taken. In FIG. 14 means is shown for simultaneously making a plurality of readings along parallel lines across the surface. As there illustrated somewhat schematically, a cross-bar or rod 125, which is suitably mounted, e.g. on a carriage (not shown) if operation is to be mechanized or automated, carries a plurality of probes 127. These are spaced longitudinally on the rod 125, on which they may be adjustably held, for example, by sliding clamps 129. The probes 127 preferably include electrolyte-carrying wheels 131 like, for example, any of those shown in FIGS. 9 to 13, but may be of other suitable design and the electrodes therein are insulated from each other by suitable means and are electrically connected by leads 133 to suitable terminals 135 on a multi-channel, recording millivoltmeter 137. An electrical connection from the terminal 139 of the latter to the specimen 141, the surface of which is to be tested, is provided by the lead 143. Thus, as the wheels 131 are rolled along the surface of the specimen, as indicated by the arrow 145, an individual record will be provided on the tape or chart 147 of the mechanogalvanic potential at successive points along the path followed by each wheel.

It will be understood that apparatus such as shown in FIG. 14 may be provided with any desired number of probes which may be spaced at any desired distances. If necessary, of course, more than one recording meter may be used. Further, while a plurality of electrolyte-carrying wheels may be manually moved over a surface by the cross bar or rod 125, either the specimen and/or the assembly of mounted wheels may be mounted on a suitably powered carriage which may be moved with reference to the other, thereby permitting automation of the testing.

The present invention is, as indicated above, useful not only in the testing of metals, including alloys, but may also be used with metalloids like germanium, carbon, silicon, and boron to determine their surface characteristics. When testing metalloids, the procedure employed is the same as with metals. For convenience in reference, the term "metal-like materials" is used herein to comprehend both metals and metalloids.

Electrode wheels such as are shown in FIGS. 11 – 13, inclusive, having a tire or rim of gelled electrolyte solution on a metal core or hub can be easily produced. The following is an example of the presently preferred procedure.

EXAMPLE 1

To 150 ml of a 0.01 M aluminum chloride solution heated to about 80° C is added 14 g of high-strength, purified gelatin. The mixture is stirred until the gelatin dissolves. Then the solution is poured into an annular mold of suitable size where it is permitted to gel or set. When removed from the mold, the gelled electrolyte tire may be placed on a core or hub of suitable metal for an electrode for use in accordance with the present invention.

If desired, the hub may form a part of the mold so that the rim and hub can be removed from the mold as a unit. In such case the hub may have means, for example, such as webs, illustrated in FIG. 13, which support the gel rim and prevent it from being accidently displaced.

It will be evident that for increased accuracy the area of the surface being tested which is contacted by the electrolyte solution should be minimized. Accordingly, the electrolyte-carrying wheels used in the practice of the present invention are preferably small in diameter and thin, although in the drawings herewith they are shown enlarged for clarity of illustration. Wheels as small as about 1.5 mm thick and about 6 mm in diameter may be used. Of course, in comparing surfaces, the MGP readings on the different specimens are preferably made with wheels of the same size.

While very satisfactory results have been obtained by the use of gelatin to produce tires of gelled electrolyte solution, it will be clear that other gelling agents may be employed if desired. Examples of usable materials are: dextrin, acacia gum, gum arabic, alginic acid, gum tragacanth, carrageenin, gum ghatti, guar gum, carboxymethylcellulose, polyvinylpyrrolidone, polyalkylene oxides, and carboxy vinyl polymers. Obviously the proportion of gelling agent to electrolyte solution will differ with different materials. However, only a small amount of experimentation will reveal usable proportions. Although larger or somewhat smaller amounts may be used, from about 3% to about 10% of gelatin is satisfactory. In addition, these or other suitable thickeners or gelling agents may be employed to thicken an electrolyte solution used for impregnating wheel tires or rims of paper, felt and the like, or used in probe wheels of sponge, porous glass, and the like, thus impeding loss of the electrolyte solution therefrom. Obviously, use of a gelling agent which reacts with the material of the electrode or the test specimen is undesirable.

It is usually desirable to employ as an electrolyte a soluble salt of the metal being tested. Most soluble salts can be used but it is preferred not to use salts which are readily decomposed or changed, for example by oxidation from the air or by hydrolysis. When a suitable salt of a metal is difficult to obtain or to handle a soluble salt of another metal, higher in the Electromotive Series than the test specimen, may be employed as the electrolyte. Thus, for example, potassium chloride has been successfully used as the electrolyte with iron and aluminum electrodes, respectively, in determining the mechanogalvanic potential of iron and aluminum surfaces. The results obtained correlated quite well with those obtained using iron sulfate and aluminum sulfate, respectively, as electrolytes. As above indicated, similar results may be obtained using soluble lithium, sodium, and calcium salts as electrolytes. The concentration of electrolyte in the solution used is not critical. Concentrations from as low as 0.0001M to as high as 1M are usable.

As above described, the use of the apparatus of the present invention is simple. In general, it is desirable to employ a test electrode which is the same in composition as that of the surface being tested and is as free from internal stress and surface contamination as practical. However, small differences in composition are not usually important except in tests where the greatest precision is required. Indeed, it has been found feasible in many cases to use as an electrode, in determining the MGP of various metal surfaces, a chemically resistive metal such, e.g. as platinum, gold, palladium, and tantalum, as well as carbon, preferably as graphite. Such materials are essentially unaffected by the electrolyte solutions used and can be employed in determining the MGP of any metal-like surface, thus serving as a "universal" electrode.

It will be evident that often for convenience and/or reduction in costs, the entire test electrode will not be in one piece, but the portion contacting the electrolyte solution will be removably secured to the main portion of the electrode. Consequently, in the apparatus of FIG. 1, the tip 33 of the electrode 28 is removable, being attached to the main body of the electrode by any suitable means such as threads, and in FIGS. 11 and 12 the core or hub 101, which is part of the probe electrode, may be formed of the same metal or metalloid as that to be tested or of one of a resistive material, such as mentioned above, suitable for use as a universal electrode. The remainder of electrode 28 in FIG. 1, and the axle 105 and shaft 107 in FIG. 12 may be of any suitable conductive metal and may be used when the probe is employed in testing any surface. It will be seen that by having the active portion, for example the tip 33 of electrode 28, of the electrode separable from the main portion thereof it is possible to easily replace a worn or corroded active portion with a new one or to use a number of active portions, each of a different material, with the same main portion in determining the MGP of different metal-like surfaces. Thus it is unnecessary to manufacture and/or store complete electrodes of the different, sometimes expensive, metals needed for tests on different materials or to use large amounts of precious metals such as platinum or gold. There is consequently a considerable saving realized.

As above stated, the present process may be employed in the testing of alloy surfaces. In such case it may be desirable to take readings of the MGP at various points on the alloy surface with different electrodes. Thus with, for example, a copper-tin alloy such as a bronze, a series of readings may be taken with a copper electrode a tin copper salt in solution as the electrolyte and another series of readings may be taken with a tin electrode and a tin salt electrolyte. The sets of readings may then be compared. In some cases it may be convenient in testing alloys to use apparatus such as shown in FIG. 14, where a number of wheel-type probes are simultaneously caused to roll across a test specimen, in which alternately arranged wheels have hubs of different alloying metals and carry as electrolyte a solution of a salt of the same metal as the hub.

It will be understood that except in tests in which the test specimen and the active portion of the electrode used are of the same metal and the electrolyte is a soluble salt of the same metal there will be present in the system a voltaic cell producing a voltage. This, however, for any specific combination will be constant and will not interfere with the mechanogalvanic potential resulting, for example, from internal stresses, the mechanogalvanic potential being merely superimposed on the base voltage.

The process of the present invention is capable of extensive use. Not only does the determination of the MGP at a number of points on the surface of a metal or metalloid give information as to the stressed condition of the surface so that the results of heat treatment, annealing, normalizing and the like can be studied or welded areas be evaluated preparatory to metal forming, but it also gives information as to the chemical uniformity of the surface. Thus differences in surface chemistry, the presence of areas which contain impurities, such as corrosion products, and areas which have been contaminated can be located and defined by the use of the present invention. Not only can the surfaces of plates or sheets be tested by the present invention, but also the surfaces of larger or smaller bodies, such as large castings or wire, and surfaces obtained by depositing a metal or metalloid on a substrate, for example by plating or vacuum deposition. It is also possible to employ the present invention on the surface of the same body before and after or during stressing of the body, for example by bending a sheet or tensioning a spring. This results in information which may be helpful in ascertaining the onset or development of fatigue and ultimate failure of the body. Tests may be carried out on either hot or cold and polished and unpolished surfaces.

Percentages stated herein are percentages by weight.

I claim:

1. A process for detecting chemical and physical irregularities in a material of the class consisting of metals and metalloids which comprises providing a probe, said probe comprising an axle, an electrode of a material of said class, and a rollable, self-supporting, non-metallic body, containing an electrolyte, carried by and rotatable with said electrode about said axle, and continuously recording the voltage, and the polarity of said voltage, generated between said electrode and the surface of a test piece of a material of said class while establishing and maintaining substantially line contact between said body and said surface by rolling said electrode and body along a path on said surface while maintaining said electrode in electrical contact with said surface through said electrolyte.

2. A process as set forth in claim 1 in which said self-supporting body is a gelled electrolyte solution.

3. A process as set forth in claim 2 in which said surface is metal and said electrolyte is a salt of a metal at least as high in the electromotive series as said surface.

4. A process as set forth in claim 2 in which said surface and said electrode are metal and said electrolyte is a salt of the metal of either said surface of said electrode.

5. A process as set forth in claim 1 in which said surface is metallic.

6. A process as set forth in claim 1 in which said surface is metalloid.

7. A process as set forth in claim 1 in which said electrode is metallic.

8. A process as set forth in claim 7 in which said surface is metal.

9. A process as set forth in claim 1 in which said electrode is metalloid.

10. A process as set forth in claim 9 in which said surface is metalloid.

11. A process as set forth in claim 1 in which the portion of said electrode contacted by said body remains constant.

12. A process as set forth in claim 1 in which said body is a firm gel comprising an electrolyte solution.

* * * * *

UNITED STATES PATENT AND TRADEMARK OFFICE
CERTIFICATE OF CORRECTION

PATENT NO. : 4,006,063

DATED : February 1, 1977

INVENTOR(S) : Minas Ensanian

It is certified that error appears in the above-identified patent and that said Letters Patent are hereby corrected as shown below:

Column 1, line 16, "idential" has been changed to -- identical --.

Column 3, line 12, "of" has been changed to -- or --.

Column 7, line 28, "potential" has been changed to -- potentials --.

Column 10, in claim 4, line 4, "of" third occurrence, has been changed to -- or --.

Signed and Sealed this

Twentieth Day of September 1977

[SEAL]

Attest:

RUTH C. MASON
*Attesting Officer*

LUTRELLE F. PARKER
*Acting Commissioner of Patents and Trademarks*